United States Patent [19]

Hamlyn et al.

[11] Patent Number: 4,665,019
[45] Date of Patent: May 12, 1987

[54] METHOD FOR MEASURING THE PLASMA LEVELS OF AN INHIBITOR OF $(Na^+ + K^+)$ ATPASE ASSOCIATED WITH HYPERTENSION AND USE IN DIAGNOSIS

[75] Inventors: John M. Hamlyn; Mordecai P. Blaustein; A. Avinoam Kowarski, all of Baltimore, Md.

[73] Assignee: University of Maryland, Baltimore, Md.

[21] Appl. No.: 528,009

[22] Filed: Aug. 31, 1983

[51] Int. Cl.[4] ............................ C12Q 1/42; C12Q 1/34
[52] U.S. Cl. ............................................ 435/21; 435/18
[58] Field of Search ........................ 424/7.1; 435/18, 21

[56] References Cited

U.S. PATENT DOCUMENTS 4,264,727  4/1981  Kolehmainen et al. ............... 435/21

FOREIGN PATENT DOCUMENTS 2027196  2/1980  United Kingdom .................. 435/21

OTHER PUBLICATIONS

British Medical Journal vol. 283, pp. 1355–1357 (1981).
Nature vol. 300, pp. 650–652 (1982).
Methods in Enzymology vol. XXIII, pp. 652–653, (1971).
Methods in Enzymology vol. IV, pp. 372–373, (1957).
J. Biological Chemistry vol. 252, No. 21, pp. 7421–7423 (1977).
Biochemistry (2nd ed.) Worth Publishers pp. 207–208.
Wardener et al., Lancet, vol. 1, (1981), pp. 411–412.
Pamnani et al., Proceedings/Interamerican Soc. Supp. II, Hypertension, vol. 3, No. 6, (1981), pp. 96–101.
Jorgensen, P., BBA, vol. 356, (1974), pp. 36–52.
Na–K–ATPase: Structure and Kinetics, Skov, J. et al., (eds.) (1979), Academic Press, pp. 405–420.
Fagan et al., Biochemistry, vol. 16, No. 1, (1977), pp. 152–158.
Sigma Chemical Company, Biochemical and Organic Compounds Cat., Feb. 1985, p. 92, A 0142.

*Primary Examiner*—Christine M. Nucker
*Assistant Examiner*—Stephen C. Wieder
*Attorney, Agent, or Firm*—Sughrue, Mion, Zinn, Macpeak and Seas

[57] ABSTRACT

A method for measuring plasma levels of an inhibitor of $(Na^+ + K^+)$ATPase associated with hypertension comprising:

(1) incubating deproteinized plasma of a patient suspected of being hypertensive in a $(Na^+ + K^+)$ATPase assay solution comprising (a) $(Na^+ + K^+)$ATPase; and (2) following the activity of the $(Na^+ + K^+)$ATPase over the course of time, and use of the method in diagnosing hypertension and in monitoring antihypertensive therapy.

83 Claims, 5 Drawing Figures

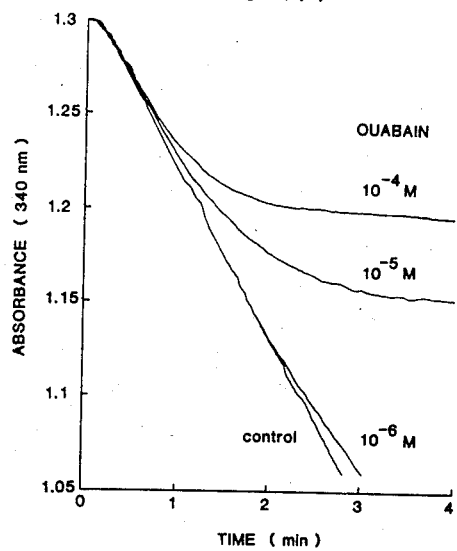
FIG. IA
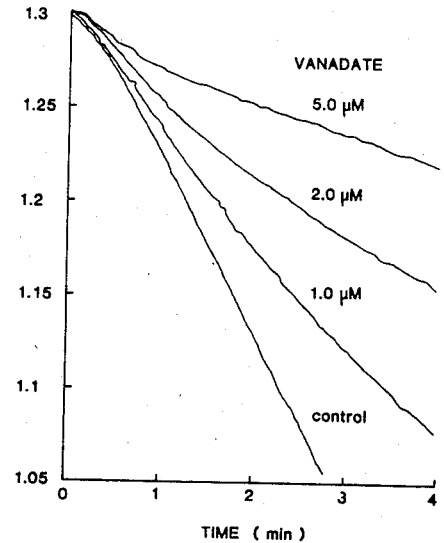
FIG. IB
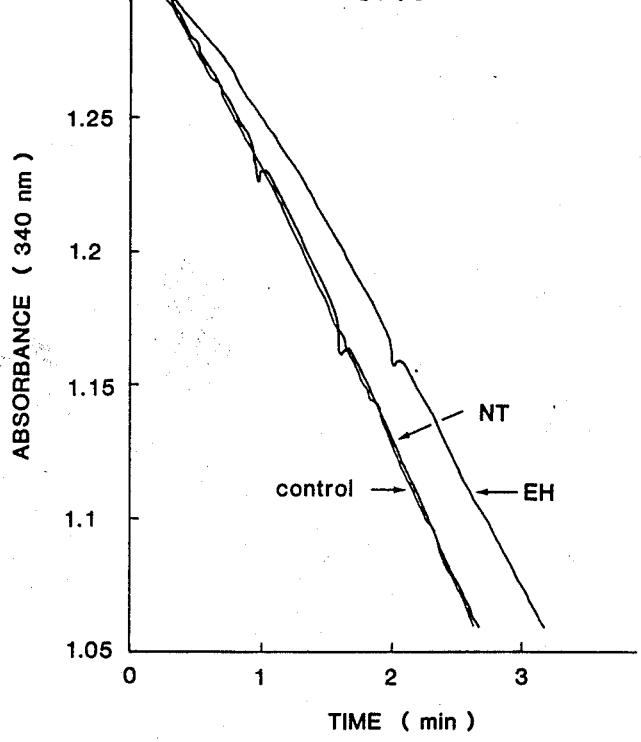
FIG. IC

METHOD FOR MEASURING THE PLASMA LEVELS OF AN INHIBITOR OF $(Na^+ + K^+)$ ATPASE ASSOCIATED WITH HYPERTENSION AND USE IN DIAGNOSIS

The development of the present invention was supported by University of Maryland, NSF (PCM-79-11704), NINCDS (NS-16106), NICHHD (HD-16077), AHA (Maryland Affiliate) and MDA.

FIELD OF THE INVENTION

The present invention relates to a method for measuring the plasma levels of an inhibitor of $(Na^+ + K^+)$ATPase that is associated with, and may, in fact, cause hypertension. More specifically, the present invention relates to a biochemical assay that measures levels of a blood-borne factor in patients, e.g., with hypertension including essential hypertension. The results obtained by this method are useful in differential diagnosis of hypertension and in monitoring patient response to therapy.

BACKGROUND OF THE INVENTION

While the aetiology of essential hypertension, a disease prevalent in cultured societies, is unknown, there is much evidence to suggest that abnormal sodium metabolism plays a critical role. That is, hypertension can be induced or exaggerated by a large sodium intake and frequently can be treated by limiting sodium intake and/or by administering natriuretics. Hypertension can also be induced by ($Na^+$ retaining) mineralcorticoids in experimental animals and in man, as a consequence of primary aldosteronism or Cushing's syndrome.

Despite the widely recognized correlation between sodium metabolism and hypertension, the underlying mechansim has escaped elucidation. However, a number of recent observations appear to provide some important clues as to these mechanisms, i.e., (1) that calcium ions are the immediate trigger for contraction in vascular smooth muscle, as in other types of muscle (see Filo, R. S.; Bohr, D. F.; and Rüegg, J. C. *Science*, 147: 1581-1583 (1972), and (2) that sodium ions play a critical role in the maintenance of calcium balance in vascular smooth muscle. (See Blaustein, M. P., *Amer. J. Physiol.*, 232: C165-C173 (1977).)

It has been postulated that in some "volume-expanded" animal models of hypertension there may be elevated plasma levels of a $Na^+$ pump inhibitor, i.e, a natriuretic hormone (see Haddy, F. J. et al, *Life Sci.* 19: 935-948 (1976).) This has led to the hypothesis that an increase in the concentration of an inhibitor of $(Na^+ + K^+)$ATPase is responsible for the increased peripheral vascular resistance in essential hypertension. That is, this inhibitor promotes both sodium and calcium gain by vascular smooth muscle, causing the increased peripheral vascular resistance which is the hallmark of hypertension. (See Folkow, B. and Neil, E., *Circulation*, Oxford University Press, pp. 560-583 (1971), and Blaustein, M. P. *Amer. J. Physiol.*, 232: C165-C173 (1977).)

Although various bioassays and cytochemical assays, as disclosed below, have been developed to detect the postulated $Na^+$ pump inhibitor in essential hypertension, no direct biochemical determination of such a circulating inhibitor has been demonstrated.

BIOASSAYS

A bioassay system has been developed which shows that the ouabain-sensitive $Na^+$ pump (the physiological equivalent of $(Na^+ + K^+)$ATPase) in white blood cells is inhibited after incubation in blood plasma from hypertensive patients (Poston, L. et al, *Brit. Med. J.*, 282: 847-849 (1981)). However, this bioassay system has disadvantages in that the incubation conditions are difficult to replicate precisely and thus the bioassay system is not clinically useful.

In another bioassay there is evidence for increased plasma levels of $Na^+$ pump inhibitors in some animal models (for example, renal and deoxycorticosterone acetate (DOCA) models) of hypertension. That is, blood plasma from animals with various forms of experimental high blood pressure (so-called "volume-expanded" hypertension) inhibit the $Na^+$ pump (ouabain-sensitive rubidium transport) in arterial smooth muscles. (See Pamnani, M. B. et al, *Hypertension* 3: Suppl. II, II-96-II-101 (1981).) However, this bioassay system has a disadvantage in that it is difficult to reproduce because the experimental conditions are not precisely defined.

A crude bioassay system has been developed for detecting the presence of a circulating $Na^+$ pump inhibitor in plasma and urine extracts using a frogskin short-circuit current (SCC) assay and an $(Na^+ + K^+)$ATPase assay. However, the SCC assay is disadvantageous in that it is a crude assay which is difficult to reproduce. Further, the $(Na^+ K^+)$ATPase inhibition data are from rat plasma samples and not human samples. In addition, the inhibition of the ouabain-sensitive fraction of the ATPase, which is the ATPase fraction whose activity is being measured in the present invention, has not been demonstrated using this bioassay. (See Kramer, H. J. *Klin. Wochenschr.* 59: 1225-1230 (1981).)

CYTOCHEMICAL ASSAYS

Two cytochemical assays have been developed which provide evidence that there is a circulating $Na^+$ pump inhibitor in hypertension. (See MacGregor, G. A. et al, *Brit. Med. J.* 283: 1335-1357 (1981) and deWardener, H. E. et al, *Lancet* i: 411-412 (1981).) However, these assays are very indirect and are not widely accepted as valid tests for the study of $Na^+$ pump activities because of uncertainties regarding quantitation. In addition, these assays have drawbacks in that they are not easily reproducible.

SUMMARY OF THE INVENTION

An object of the present invention is to provide a method which can be used to measure a $Na^+$ pump inhibitor found in the blood plasma of patients having hypertension, including essential hypertension.

A further object of the present invention is to provide a method which can be used to differentially diagnose hypertension.

A still further object of the present invention is to provide a method which can be used to monitor patient response to antihypertensive therapy.

An additional object of the present invention is to provide a method for measuring endogenous inhibitors of ouabain-sensitive $(Na^+ + K^+)$ATPase.

Another object of the present invention is to provide a direct biochemical assay for quantitating levels of a $Na^+$ pump inhibitor in patients with hypertension that is both reproducible and clinically and diagnostically useful.

A further object of the present invention is to facilitate the development of a method for isolating and characterizing the Na+ pump inhibitor associated with patients with hypertension as well as other endogenous inhibitors of the ouabain-sensitive (Na++K+)ATPase.

A still further object of the present invention is to provide a workable assay for use in purification of the inhibitor of the Na+ pump found in patients having hypertension.

The above-described objects of the present invention have been met by the method of this invention which comprises:
(1) incubating deproteinized plasma from a patient suspected of being hypertensive in a (Na++K+)ATPase assay solution comprising (a) (Na++K+)ATPase; and
(2) following the activity of the (Na++K+)ATPase over the course of time.

Another aspect of this invention involves a method for diagnosing hypertension comprising:
(1) incubating deproteinized plasma of a patient suspected of being hypertensive in a (Na++K+)ATPase assay solution comprising (a) (Na++K+)ATPase;
(2) following the activity of the (Na++K+)ATPase over the course of time; and
(3) comparing the activity in step (2) with the (Na++K+)ATPase activity of a standard.

A further aspect of this invention involves a method for monitoring antihypertensive therapy comprising:
(1) incubating deproteinzied plasma of an anti-hypertensive patient in a (Na++K+)ATPase assay solution comprising (a) (Na++K+)ATPase;
(2) following the activity of the (Na++K+)ATPase over the course of time;
(3) comparing the (Na++K+)ATPase activity of step (2) with the (Na++K+)ATPase activity of a standard; and
(4) repeating steps (1)–(3) at suitable time intervals after the initiation of therapy and monitoring the activity of the (Na++K+)ATPase at each time interval.

BRIEF DESCRIPTION OF THE DRAWINGS

FIG. 1 illustrates inhibition of (Na++K+)ATPase activity by the known inhibitors, ouabain (FIG. 1a) and vanadate (FIG. 1b), and by plasma samples (FIG. 1c).

DETAILED DESCRIPTION OF THE INVENTION

Figure 2:
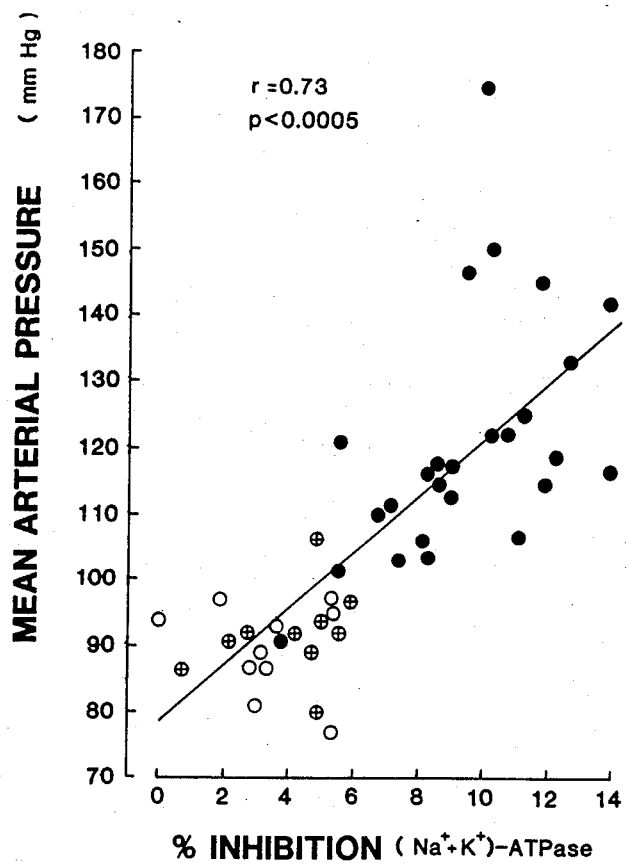
FIG. 2 illustrates the relationship between mean arterial blood pressure (MAP) and inhibition of (Na++K+)ATPase by plasma samples from normotensive and hypertensive individuals.

The present invention provides a direct biochemical assay for detecting elevated levels of a circulating (Na++K+)ATPase inhibitor in the blood plasma of patients suspected of having hypertension, thereby permitting diagnosis of hypertension and monitoring therapy. The method comprises (1) incubating deproteinized plasma of a patient in a (Na++K+)ATPase assay solution comprising (a) (Na++K+)ATPase, and (2) following the activity of the (Na++K+)ATPase over the course of time.

The activity of the (Na++K+)ATPase may be followed by any suitable means. For example, the activity of the (Na++K+)ATPase may be followed by measuring the concentration of a reaction product, e.g., inorganic phosphate, of the (Na++K+)ATPase reaction or the activity of the (Na++K+)ATPase may be coupled to an oxidation-reduction reaction and the changes in this reaction can be measured.

In one embodiment of the process of this invention, the assay comprises (1) incubating deproteinized plasma from a patient who is to be diagnosed in a solution comprising (a) (Na++K+)ATPase and (2) following the release of inorganic phosphsate as a consequence of ATP hydrolysis.

In a second embodiment of the process of this invention, the assay comprises (1) incubating deproteinized plasma from a patient who is to be diagnosed in a solution comprising (a) (Na++K+)ATPase and (b) an enzymatic ATP coupled oxidation-reduction reaction system; and (2) following changes in the enzymatic ATP coupled oxidation-reduction reaction system by measuring a coenzyme employed therewith or another substance whose spectroscopic properties are changed during the reaction.

In a third embodiment of the process of this invention, the assay comprises (1) incubating deproteinized plasma from a patient who is to be diagnosed in a solution comprising (a) (Na++K+)ATPase, (b) an enzymatic ATP coupled oxidation-reduction reaction system, and (c) an enzymatic ATP regenerating reaction system; and (2) following changes in the enzymatic ATP coupled oxidation-reduction reaction system by measuring a coenzyme employed therewith or any other during the reaction.

Deproteinized plasma employed in the present invention as the sample for assay may be produced by deproteinizing plasma by conventional means, e.g., as described in Gruber, K. A., et al, *Nature* 287: 743–745 (1980). This method of deproteinizing the plasma involves first acidifying the plasma to a pH of 5.0 to 5.6; next boiling the resulting slurry for 1 to 5 minutes and then centrifuging the resulting slurry to remove the protein precipitate and recover the plasma supernatant. Other methods of deproteinization, involving, for example, ultrafiltration, column chromatography, tricloracetic acid, perchloric acid, ammonium sulfate, may be used, although the ATPase assay conditions will then require appropriate modifications to accept the samples treated by these procedures. These modifications involve adjustment of either the pH and/or electrolyte contents of the deproteinized plasma such that the deproteinized plasma can be introduced into the ATPase assay. Usually, these modifications can be accomplished by addition of organic bases and/or solutions of inorganic salts to the deproteinized plasma so as to reproduce the effective ATPase assay conditions in accordance with the principles of Example 2.

It should be apparent to one skilled in the art that the assay conditions set forth in Example 2 are preferred to optimize the ATPase assay and minimize the errors that may result from assay of plasma samples of slightly varying composition. However, it will also be recognized by one skilled in the art that, as long as the plasmas and standards are assayed under substantially similar conditions, the method of this invention can be practiced in all of its aspects.

The incubation temperatures employed in the process of the present invention will vary depending on the enzymes employed. A suitable temperature range will be from about 10° to about 50° C., preferably 30° to 37° C.

Any source of $(Na^+ + K^+)$ATPase as component (a) of the assay solution may be used in the present invention including $(Na^+ + K^+)$ATPase derived from dogs, pigs, sharks, eels, shrimp and cows. Canine (dog) kidney derived $(Na^+ + K^+)$ATPase is preferably employed.

In the first embodiment of the present invention, Pi release can be measured using $\gamma$-$^{32}$P-labelled ATP to follow the ATPase reaction under appropriate conditions, by first quenching and then extracting and counting the liberated $^{32}$Pi. An example of such a method is described in Salem, N., et al., Biochim. Biophys. Acta 641: 366-376 (1981).

An alternative method for measuring Pi release involves the estimation of released Pi by a colorimetric assay, for example, the reduction of phosphomolybdate complex by A.N.S. (1:2:4-amino-naphtholsulfonic acid) (King, E. J., Biochem. J. 26:292-297 (1926)), or by iron (Tavssky, H. H., and Shorr, E., J. Biol. Chem. 202: 675-685 (1953)), or by malachite green (Carter, S. G., and Karl, D. W., J. Biochem. Biophys. Methods 7: 7—13 (1982)), or by ascorbate or other appropriate reducing agents.

The $\gamma$-$^{32}$Pi-labelled ATP release method can be adapted to the plasma $(Na^+ + K^+)$ATPase inhibitor assay, described in detail in the examples below, with minimal modification. However, the methods that involve the use of colorimetric techniques to determine Pi release from ATP require additional modification because of the presence of high levels of Pi in blood plasma, i.e., the endogenous Pi would have to be removed, by ion exchange chromatography or dialysis, for example, before the deproteinized plasma could be used in this type of assay system.

Any enzymatic ATP coupled oxidation-reduction reaction system as component (b) may be employed in the assay solution of the second and third embodiments of the present invention including pyruvate-lactate dehydrogenase (LDH), pyruvate-pyruvate decarboxylase (PDC), acetaldehyde-alcohol dehydrogenase (ADH), pyruvate-pyruvate dehydrogenase (PDH) or glyceraldehyde-3-phosphate-glyceraldehyde phosphate dehydrogenase (GAPD). The preferred enzymatic ATP coupled oxidation-reduction system is pyruvate-lactate dehydrogenase.

Furthermore, any enzymatic ATP regenerating reaction system as component (c) may be used in the assay solution of the third embodiment of the present invention including phosphoenolpyruvate-pyruvate kinase or 1,3-diphosphoglycerate-phosphoglycerate kinase. Phosphoenolpyruvate-pyruvate kinase is the preferred enzymatic ATP generating system.

In the second and third embodiments of the present invention, changes in the enzymatic ATP coupled oxidation-reduction reaction system may be followed by any appropriate measuring means such as measuring the concentration of a coenzyme or any other coupled substance such as a chromophore, fluorophore, etc., to be employed therewith using changes which occur in ultraviolet light or visible light absorbance, fluorescence, excitation-emission spectra or absorbance of chromophores.

Ultraviolet light absorbance at or near the optimum absorbance wavelength of the coenzyme employed, is the preferred measuring means. For example, when NADH is the coenzyme to be measured, the ultraviolet light absorbance is measured most conveniently at 340 nm. When NAD is the coenzyme to be measured, the ultraviolet light absorbance is measured at 250 nm.

The coenzyme, which may inherently act as a chromophore, fluorophore, etc., or the coupled chromophore, fluorophore, etc., to be measured will depend ultimately upon the enzymatic ATP coupled oxidation-reduction reaction system employed. For example, NADH, NAD, NADPH, NADP or FAD may be employed as the coenzyme. NADH is the preferred coenzyme to be measured in the present invention. Examples of chromophores useful in the present invention include methylene blue, NADH, NADPH, etc. Examples of fluorophores useful in the present invention include NADH, NADPH, NAD, NADP, etc.

While the period of time in which the progress of the enzymatic ATP coupled oxidation-reduction reaction system is measured will vary depending on the activity of the enzymes employed in the $(Na^+ + K^+)$ATPase assay system, a typical time period will be about 2-5 minutes, but may be adjusted to periods as long as an hour or more, or a few seconds or less.

For example, a slower than normal decrease in the concentration of the coenzyme substrate or coupled substance to be measured, as compared with a suitably prepared standard, indicates the presence of the ATPase inhibitor associated with hypertension. Alternatively, a slower than normal increase in the concentration of the coenzyme product or product of a reaction occurring from the coupled substance to be measured, due to the presence of the inhibitor, as compared with a suitably prepared standard, indicates the presence of the ATPase inhibitor associated with hypertension.

Examples of the standard can include plasma from a normotensive person, with or without the addition of at least one inhibitor of $(Na^+ + K^+)$ATPase; or an artificial plasma saline solution, with or without the addition of at least one inhibitor of $(Na^+ + K^+)$ATPase. Examples of known inhibitors include ouabain, vanadate, quercetin and N-ethylmaleimide.

The artificial plasma saline solution comprises an appropriate physiological saline solution, for example, a PSS comprising: 2.1 mM KCl; 120 mM NaCl; 26 mM $NaHCO_3$; 2.5 mM $CaSO_4$; 1.2 mM $K_2HPO_4$; 1.2 mM $MgSO_4$; 3.4 mM EGTA; 2.8 mM EDTA; and 800 µg/ml bovine serum albumin.

When monitoring antihypertensive therapy, a suitable monitoring interval may be daily or weekly or any other suitable interval.

The assay system employed in the third embodiment of the present invention is a modification of the $(Na^+ + K^+)$ATPase coupled oxidation-reduction reaction system described in Fagan, J. B. and Racker, E., Biochem. 16:152-158 (1977).

An example of the second embodiment of the present invention wherein ATP is not regenerated includes the use of glyceraldehyde-phosphate dehydrogenase. This embodiment can be schematically illustrated by reaction (A) below:

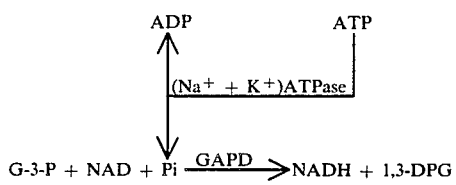

$$\text{G-3-P} + \text{NAD} + \text{Pi} \xrightarrow{\text{GAPD}} \text{NADH} + 1{,}3\text{-DPG} \qquad \text{Reaction (A)}$$

This assay is useful over relatively short time periods, i.e., 10 to 60 seconds. The reaction may be monitored conveniently by recording the increase of absorbance at 340 nm in order to follow the formation of NADH over the course of time. The rate of formation of NADH is obtained from the linear portion of the recording, and the ATPase activity can then be computed. Due to the presence of endogenous Pi in the plasma samples, large quantities of G-3-P and NAD are required. In addition, the 1,3-DGP formed is unstable, and tends to decompose; this liberates Pi which is then available to re-enter the reaction.

In the third embodiment of the present invention, the enzymatic generation of ATP is coupled to the oxidation of NADH so that the action of various inhibitors can be monitored by continuously recording the absorbance of NADH at 340 nm. A slower than normal decrease in the concentration of NADH, i.e., higher absorbance and/or change in fluorescence or other spectrophotographic properties, indicates the presence of an inhibitor of ATPase since the presence of the inhibitor indirectly inhibits the oxidation of NADH by inhibiting the production of the substrate to be employed therewith, e.g., pyruvate or acetaldehyde. This embodiment can be schematically illustrated by reactions (B) and (C) below:

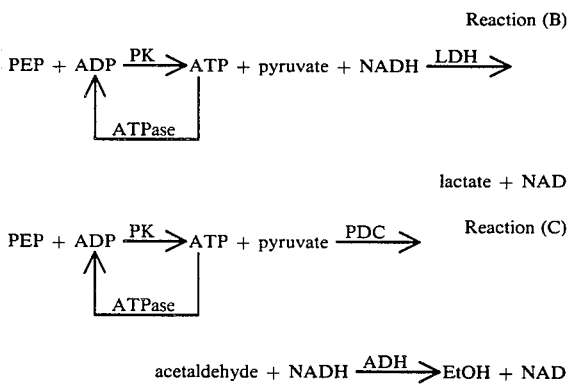

In addition, in the third embodiment of the present invention, the enzymatic generation of ATP can be coupled to the reduction of NAD so that the action of various inhibitors can be monitored by continuously recording the absorbance of NAD at 250 nm. A slower than normal decrease in the concentration of NAD, i.e., higher absorbance and/or change in fluorescence or other spectroscopic properties, indicates the presence of the inhibitor since the inhibitor indirectly inhibits the reduction of NAD by inhibiting the production of the substrate to be employed therewith, e.g., pyruvate or inorganic phosphate. This embodiment can be schematically illustrated by reactions (D) and (E) below:

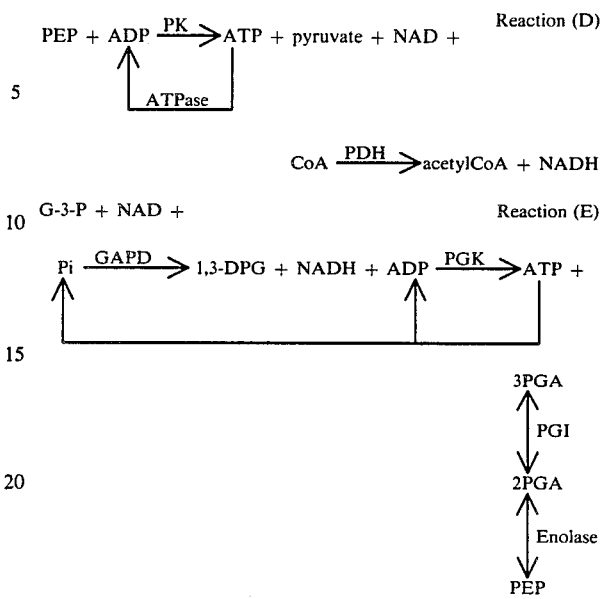

In reaction (E) above the abbreviations are defined as follows:

G-3-P = glyceraldehyde-3-phosphate
GAPD = glyceraldehyde phosphate dehydrogenase
1,3-DPG = 1,3-diphosphoglycerate
PGK = phosphoglycerate kinase
3PGA = 3-phosphoglyceric acid
PGI = phosphoglycerarte isomerase
2PGA = 2-phosphoglyceric acid
PEP = phosphoenol pyruvate The following examples are illustrative of the present invention and are in no way intended to limit the scope thereof.

EXAMPLE 1

The activity of the humoral inhibitor of $(\text{Na}^+ + \text{K}^+)$ATPase was compared with the behavior of two well characterized inhibitors of ATPase, i.e., ouabain and vanadate. The measurement of the inhibition of $(\text{Na}^+ + \text{K}^+)$ATPase activity was carried out in the following manner.

The $(\text{Na}^+ + \text{K}^+)$ATPase preparation employed in the assay of this example comprised unsealed membrane sheets as described in Jorgensen, P. L. *Biochim. Biophys. Acta* 356: 36–52 (1974). Thus, it was not able to distinguish between an external and an internal site of action for the inhibitor.

The data below indicate that the inhibitor of $(\text{Na}^+ + \text{K}^+)$ATPase associated with hypertension, in this case essential hypertension, must bind more rapidly than ouabain.

The ATPase assay solution employed contained 400 μl of an ATPase cocktail and 580 μl of water. The ATPase cocktail was such that the final reaction conditions were (in 1.0 ml) as follows: 20 mM KCl; 100 mM NaCl; 4.5 mM MgSO$_4$; 5 mM EGTA; 3 mM Na$_2$ATP; 1.2 mM tricyclohexylammonium phosphoenolpyruvate (PEP), 0.25 NADH, 40 mM trimethylaminoethanesulphonic acid (TES)-Tris, pH 7.4; 1.2 units lactate dehydrogenase (LDH); and 1.2 units pyruvate kinase (PK), (ATP, PEP, NADH, LDH and PK were purchased from Boehringer Mannheim Biochemicals; LDG and PK enzymes were obtained as glycerol suspensions.)

The (Na$^+$+K$^+$)ATPase suspension was prepared for assay by suspending canine kidney (Na$^+$+K$^+$)AT-Pase (obtained from Sigma Chemical having a specific activity of 5-6 μmol per min per mg protein and containing a ouabain-insensitive Mg$^{2+}$-ATPase activity which was less than 2% of the total steady-state ATPase activity) in 500 μM Na$_4$EDTA, 10 mM (TES)-Tris pH 7.4, at a protein concentration of 150 μg/ml. The resuspended enzyme was incubated at 25° C. for 3 hours and then stored on ice. The activity of the ATPase thus prepared does not change by more than 1% during the following 20 hours on ice.

The assay was initiated by the rapid addition of 20 μl of ATPase suspension (3 μg protein) to 980 μl of ATPase assay solution in a 1.0 ml cuvette at 37° C. The decrease in ultraviolet light absorbance at 340 nm (A$_{340}$) due to NADH oxidation ($\epsilon = 6.22 \times 10^3$ 1 mol$^{-1}$ cm$^{-1}$) was continuously recorded using a Beckman Model 25 UV-VIS recording spectrophotometer.

The results obtained are shown in FIG. 1. FIG. 1a illustrates ATPase inhibition by ouabain. Ouabain was prepared as stock solutions in dimethyl sulfoxide, (DMSO) and was added as 1 μl aliquots to the ATPase assay solution to give the final concentrations indicated in FIG. 1a. The control contained an appropriate quantity of DMSO.

The data in FIG. 1a demonstrate that this cardiotonic steroid has no significant effect on the reaction for the first 30 seconds, and thereafter causes a progressive, dose-dependent increase in inhibition.

This confirms past studies which have shown that ouabain and other cardiotonic steroids inhibit (Na$^+$+K$^+$)ATPase in a dose-dependent manner when measuring the release of inorganic phosphate (see Akera, T. et al, in *Na, K-ATPase, Structure and Kinetics*, Norby, J. G. and Skou, J. C., Eds., pages 405-420, Academic Press, New York (1979)).

FIG. 1b illustrates ATPase inhibition by vanadate. In this reaction, vanadate, as Na$_3$VO$_4$, was freshly prepared in water and pre-added to the reaction solution. The control contained in appropriate quantity of water.

The data in FIG. 1b demonstrate that inhibition of ATPase increased with time as has been previously demonstrated in Quist, E. E. and Hokin, L. E., *Biochim. Biophys. Acta* 511: 202-212 (1978) and Cantley, L. C. et al, *J. Biol. Chem.* 252: 7421-7423 (1977). Since a much faster association rate constant for binding exists with vanadate than with ouabain, the effect of vanadate was apparent in the first few seconds of the reaction, especially at higher concentrations.

By measuring the steady-state levels of (Na$^+$+K$^+$)ATPase activity in the presence of various vanadate concentrations, it has been estimated that the K$_i$ is 0.9 μM which is in reasonable agreement with published values in Quist, supra, and Cantley, supra.

Neither ouabain nor vanadate, at the concentrations shown in FIGS. 1a and 1b, had a significant effect on the efficacy of the ATP generating reaction system, as determined by inspection of the rates of NADH oxidation in response to the addition of 10-50 μM ADP. The activity of the ATP generating system was found to be over 70-fold greater than that of the total ATPase activity under these conditions.

FIG. 1c illustrates the kinetic behavior of (Na$^+$+K$^+$)ATPase assayed in the presence of a saline solution (control) and deproteinized plasma samples derived from one normotensive individual and from a patient with essential hypertension. The assay in FIG. 1c was conducted in a similar manner to that used for FIGS. 1a and 1b except that the ATPase assay solution included: 9 mM MgSO$_4$ and 2 mM CaCl$_2$. Further, 500 μl of water were replaced by an equivalent volume of deproteinized plasma obtained from a normotensive individual or a patient with essential hypertension. The control contained, in addition to the assay cocktail, 500 μl of a solution of the following composition: 2.1 mM KCl; 120 mM NaCl; 26 mM NaHCO$_3$; 2.5 CaSO$_4$; 1.2 mM K$_2$HPO$_4$; 1.2 mM MgSO$_4$; 3.4 mM EGTA; 2.8 mM EDTA; and 800 μg/ml bovine serum albumin. The EDTA and EGTA were used to control for the presence of anticoagulants in the plasma samples.

Plasma samples were analyzed for: Na$^+$ and K$^+$ by flame photometry; inorganic phosphate as in King, E. J., *Biochem J.* 26: 292-297 (1932); and protein content as in Bradford, M. M., *Analyt. Biochem.* 72: 248-254 (1976).

The plasma samples were stored at $-20°$ C. and subsequently deproteinized by acidification to pH 5.5 with 1.0M HCl and boiled for 2 minutes. The resultant slurry was centrifuged at 30,000 g for 30 minutes at 4° C., and the clear supernatant was removed for electrolyte and protein content determinations as described above. The protein removal was typically 99%, giving a final protein content of 800±180 μg/ml in the supernatants.

As FIG. 1c demonstrates, about 1.5 minutes were required to reach a steady state of enzyme activity, which lasted for at least 10 minutes (not shown). The normotensive plasma (NT) in this example produced no inhibition of activity compared with the control. In contrast, the hypertensive sample (EH) produced a 14% inhibition of steady-state activity which remained constant for the next 10 minutes of the reaction period. This result demonstrates the presence of an increased level of an inhibitor of (Na$^+$+K$^+$)ATPase in hypertensive plasma that has a rapid onset of action in contrast to inhibition with ouabain which is not rapid.

The curves in FIGS. 1a, 1b and 1c were traced from original data.

EXAMPLE 2

FIG. 2 demonstrates the relationship between mean arterial blood pressure (MAP) and inhibition of (Na$^+$+K$^+$)ATPase by plasma samples from normotensive and hypertensive individuals. Of the 46 individuals used in the study, 20 were normal subjects (ages 34±14 years, range 21-66 years) and 26 patients (ages 49±11 years, range 32-67 years) suffering from essential hypertension. All of the hypertensive patients were males, 18 were black. Twelve of the normotensive patients were males; 6 were black. None of the normotensive patients had known endocrine abnormalities and none of the hypertensive patients showed any evidence of end-organ damage or serious intercurrent disease. All of the patients with essential hypertension had blood pressure higher than the 95th percentile for their age and sex on at least three previous office visits and had received no drug therapy for at least two weeks before the study. Thirty-six individuals, including all of the patients with hypertension, were characterized endocrinologically using integrated hormone profiling based on the principle of continuous 6-hour blood withdrawal as described in Zadik, Z. et al, *J. Clin. Endocrin. Metab.* 50: 842-845 (1980) and Kowarski, A. A. et al, *Johns Hopkins Med. J.* 142: 35-38 (1978). The rationale for the collection protocol is discussed in Zadik et al, supra.

Plasma samples were collected continuously for 6 hours using an indwelling non-thrombogenic catheter connected to a constant withdrawal pump. A sample (10 ml) was collected every 30 minutes into glass tubes containing (final concentrations) 2.8 mM EDTA, 3.4 mM EGTA and 2.6 mM glutathione on ice. Cells and plasma were separated by immediate centrifugation and the plasma was stored on ice. After the six-hour withdrawal, aliquots of the 30-minute samples were combined to give a six-hour integrated pool. Plasma renin activity, aldosterone, cortisol, noradrenaline and adrenaline were measured as described in Zadik et al, supra, and Kowarski et al, supra. No significant correlation was found between the levels of these substances and blood pressure. The plasma samples were deproteinized and their $(Na^+ + K^+)$ATPase inhibiting activity was determined as in Example 1.

The final electrolyte composition of the ATPase solution varied because of the addition of the plasma samples. Thus, the final assay conditions varied as follows: 22–23 mM $K^+$; 170–175 mM $Na^+$; 3.25–4.5 mM total $Ca^{2+}$; $<10^{-7}$M free $Ca^{2+}$; 9.5–9.6 mM total $Mg^{2+}$; 2.1–2.8 mM free $Mg^{2+}$; 6.7 mM total EGTA, 2.2–100 μM free EGTA; 1.4–2.1 mM total EDTA; $<10^{-8}$M free EDTA; 3 mM total ATP; $<10^{-7}$M free ATP; and 0.4–0.6 mM $PO_4^{3-}$.

The controlled variation of 20–30 mM $K^+$; 100–200 mM $Na^+$; 1–500 μM free EGTA; 2–2.8 mM free $Mg^{2+}$; and 0.4–0.6 mM $PO_4^{3-}$ gave no more than a 2% change in the steady-state activity of $(Na^+ + K^+)$ATPase. High concentrations ($>10^{-4}$M) of free $Ca^{2+}$ and ATP are both potent inhibitors of the ATPase but, due to the presence of excess EGTA and $Mg^{2+}$, respectively, free $Ca^{2+}$ is reduced to non-interfering levels in the assay of the present invention. In addition, the excess EGTA serves to chelate other trace elements that may interfere with the assay. Given these and other considerations, the cumulative error for each determination of ATPase activity was estimated to be less than 3%.

Percent inhibition was calculated as:

$$100 - \frac{\text{Sample } \Delta A_{340}/\text{min}}{\text{Control } \Delta A_{340}/\text{min}} \times 100.$$

The uncertainty of the error of the ATPase activity and the variability of blood pressure could contribute to the scatter pattern observed in FIG. 2, wherein ● corresponds to 6-hour integrated samples collected from patients with essential hypertension, ⊕ corresponds to the 6-hour integrated samples collected from normotensive patients and O corresponds to discrete single samples collected from normotensive patients. The regression line in FIG. 2 was fitted by the least-square method. The correlation between mean arterial blood pressure (MAP) and percent inhibition is highly significant ($r=0.73$, $P<0.0005$).

Systolic and diastolic blood pressures were measured at hourly intervals during blood collections, and the results were averaged. Mean arterial pressure was measured as: MAP=0.33×pulse pressure+diastolic pressure.

A significant correlation between MAP and $(Na^+ + K^+)$ATPase inhibition was found when the hypertensive group alone was analyzed ($r=0.46$, $P<0.01$); no significant correlation was found for the normotensive group. However, inclusion of the normotensives in the overall analysis resulted in a greater correlation coefficient and significance values ($r=0.73$, $P<0.0005$). Slightly smaller correlation coefficients ($r=0.69$ and 0.68, respectively), but similar P values, were obtained when data from blacks and whites were evaluated separately. The correlation was similar ($r=0.77$, $P<0.0005$) when diastolic pressure was used instead of MAP.

Although the above results were obtained on male patients, the assay of the present invention is equally applicable to females. One of the previously diagnosed hypertensive patients was normotensive on the day of blood withdrawal (MAP=91 mm Hg); plasma samples from this individual exhibited a low ($<4\%$) $(Na^+ + K^+)$ATPase inhibition.

The maximal inhibition observed in this example was 14%. This is an underestimation of the inhibition expected in vivo because the plasma samples were diluted two-fold in the assay. The apparent inhibitory activity represents an effect on $(Na^+ + K^+)$ATPase per se, because the contribution of ouabain-insensitive $Mg^{2+}$-ATPase to the total steady-state hydrolysis of ATP is less than 2% under the conditions employed.

EXAMPLE 3

An endogenous digoxin-like material has been reported to exist in the plasma of volume-expanded dogs (see Gruber, K. A. et al, *Nature* 287: 743–745 (1980)) and hypertensive monkeys (see Gruber, K. A. et al, *Hypertension*, 4: 348–354 (1982)). The plasma samples of the 46 patients of Example 2 were thus tested for digoxin-like immunoreactivity. This substance has been postulated to be an endogenous ligand for the cardiac glycoside binding site of the $Na^+$ pump. The action of such a substance may therefore be related to inhibition of $Na^+$ transport and elevation of cellular $Na^+$ as described in essential hypertension (see Losse, H. et al, *Klin. Wschr.* 38: 393–395 (1960) and Edmondson, R. P. S. et al, *Lancet* i, 1003–1005 (1975)).

Determination of MAP and inhibition of $(Na^+ + K^+)$ATPase was conducted as described above. Red blood cell $Na^+$ content was determined on freely collected cells by atomic absorption spectroscopy after washing the cells three times in isotonic $MgCl_2$, determination of haematocrit and lysis of the cells in deionized water. Subsequent dilutions were performed in CsCl.

For technical reasons, 34 of the red blood cell $Na^+$ determinations were performed on cells from individuals other than those tested for $(Na^+ + K^+)$ATPase inhibition and digoxin-like immunoreactivity. However, all of the blood samples were obtained from individuals in the same populations as those identified for the study. Plasma digoxin equivalents were determined by digoxin radioimmunoassay (purchased from New England Nuclear) essentially as described by Gruber, K. A. et al, *Nature* 287: 743–745 (1980).

Deproteinized plasma samples were lyophilized and resuspended to 10× their original concentration in water and assayed for their ability to compete with iodinated digoxin for a digoxin-specific antibody. Some samples were seeded with digoxin to insure that the antibody was not affected by the increased electrolyte content of the assay.

Figure 3:
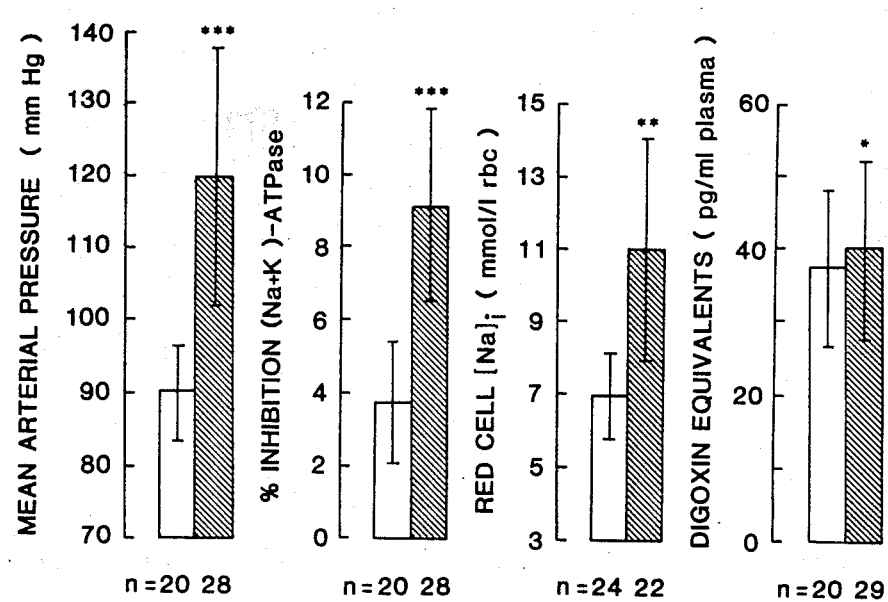
FIG. 3 illustrates mean levels of MAP, red blood cell Na+ levels, percent (Na++K+)ATPase inhibition, and digoxin-like immunoreactivity in plasma samples of normotensive and hypertensive individuals.

The data presented in FIG. 3 are corrected for concentration and dilution factors incurred during sample preparation and are described as pg digoxin equivalents per ml of plasma. None of the individuals had received cardiac glycosides. The values shown in FIG. 3 are mean±standard deviations of the indicated number of samples. Significance of the differences in the means was determined by Student's t-test. In FIG. 3 * equals $P<0.0005$;  equals $P<0.005$; * equals $P>0.1$, i.e. not significant.

As the data in FIG. 3 demonstrate, the mean essential hypertensive MAP was more than two standard deviations above the mean normotensive MAP. Further, the mean percent inhibition of $(Na^+ +K^+)$ATPase was significantly elevated in the essential hypertensive group as well as the intracellular erythrocyte $Na^+$ content.

In addition, as illustrated in FIG. 3, it was not possible to demonstrate a significant elevation of digoxin-like immunoreactivity in the plasma samples that inhibited the $(Na^+ +K^+)$ATPase. Thus, there is no correlation between the two assays which suggests that the $(Na^+ +K^+)$ATPase inhibitor and the digoxin-like substance are not related.

While this invention has been described in detail with reference to specific embodiments thereof, it would be apparent to one skilled in the art that various changes and modifications can be made therein without departing from the spirit and scope thereof.

We claim:

1. A method for measuring the plasma levels of an inhibitor of $(Na^+ +K^+)$ATPase associated with hypertension comprising:
   (1) incubating a deproteinized plasma sample from a patient in a $(Na^+ +K^+)$ATPase assay solution comprising ATP and (a) $(Na^+ +K^+)$ATPase; and
   (2) following the activity of the $(Na^+ +K^+)$ATPase over the course of time so as to measure the plasma levels of said inhibitor.

2. The method for measuring the plasma levels of an inhibitor of $(Na^+ +K^+)$ATPase associated with hypertension as in claim 1, wherein said (a) $(Na^+ +K^+)$ATPase is selected from the group consisting of canine kidney $(Na^+ +K^+)$ATPase, bovine kidney $(Na^+ +K^+)$ATPase, porcine kidney $(Na^+ +K^+)$ATPase, bovine brain $(Na^+ +K^+)$ATPase, shark $(Na^+ +K^+)$ATPase, eel $(Na^+ +K^+)$ATPase and shrimp $(Na^+ +K^+)$ATPase.

3. The method for measuring the plasma levels of an inhibitor of $(Na^+ +K^+)$ATPase associated with hypertension as in claim 1, wherein said (a) $(Na^+ +K^+)$ATPase is canine kidney $(Na^+ +K^+)$ATPase.

4. The method for measuring the plasma levels of an inhibitor of $(Na^+ +K^+)$ATPase associated with hypertension as in claim 1, wherein the activity of (a) $(Na^+ +K^+)$ATPase is followed by measuring the release of inorganic phosphate as a consequence of ATP hydrolysis.

5. The method for measuring the plasma levels of an inhibitor of $(Na^+ +K^+)$ATPase associated with hypertension as in claim 4, wherein the release of inorganic phosphate as a consequence of ATP hydrolysis is followed using $\gamma$-$^{32}$Pi-labelled ATP and measuring the liberated $^{32}$Pi.

6. The method for measuring the plasma levels of an inhibitor of $(Na^+ +K^+)$ATPase associated with hypertension as in claim 4, wherein the release of inorganic phosphate as a consequence of ATP hydrolysis is followed by a colorimetric assay.

7. The method for measuring the plasma levels of an inhibitor of $(Na^+ +K^+)$ATPase associated with hypertension as in claim 4, wherein said (a) $(Na^+ +K^+)$ATPase is selected from the group consisting of canine kidney $(Na^+ +K^+)$ATPase, bovine kidney $(Na^+ +K^+)$ATPase, porcine kidney $(Na^+ +K^+)$ATPase, bovine brain $(Na^+ +K^+)$ATPase, shark $(Na^+ +K^+)$ATPase, eel $(Na^+ +K^+)$ATPase and shrimp $(Na^+ +K^+)$ATPase.

8. The method for measuring the plasma levels of an inhibitor of $(Na^+ +K^+)$ATPase associated with hypertension as in claim 4, wherein said (a) $(Na^+ +K^+)$ATPase is canine kidney $(Na^+ +K^+)$ATPase.

9. The method for measuring the plasma levels of an inhibitor of $(Na^+ +K^+)$ATPase associated with hypertension as in claim 1, wherein said $(Na^+ +K^+)$ATPase assay solution additionally comprises (b) an enzymatic ATP coupled oxidation-reduction reaction system; and the method comprises following the activity of $(Na^+ +K^+)$ATPase by following changes in the enzymatic ATP coupled oxidation-reduction reaction system by measuring the concentration of a coenzyme or any other substance employed therewith whose spectroscopic properties are changed during the reaction.

10. The method for measuring the plasma levels of an inhibitor of $(Na^+ +K^+)$ATPase associated with hypertension as in claim 9, wherein said (a) $(Na^+ +K^+)$ATPase is selected from the group consisting of canine kidney $(Na^+ +K^+)$ATPase, bovine kidney $(Na^+ +K^+)$ATPase, porcine kidney $(Na^+ +K^+)$ATPase, bovine brain $(Na^+ +K^+)$ATPase, shark $(Na^+ +K^+)$ATPase, eel $(Na^+ +K^+)$ATPase and shrimp $(Na^+ +K^+)$ATPase.

11. The method for measuring the plasma levels of an inhibitor of $(Na^+ +K^+)$ATPase associated with hypertension as in claim 9, wherein said (a) $(Na^+ +K^+)$ATPase is canine kidney $(Na^+ +K^+)$ATPase.

12. The method for measuring the plasma levels of an inhibitor of $(Na^+ +K^+)$ATPase associated with hypertension as in claim 9, wherein said enzymatic ATP coupled oxidation-reduction reaction system (b) is glyceraldehyde-3-phosphate-glyceraldehyde-phosphate dehydrogenase.

13. The method for measuring the plasma levels of an inhibitor of $(Na^+ +K^+)$ATPase associated with hypertension as in claim 9, wherein said coenzyme is selected from the group consisting of NADH, NAD, NADPH, NADP, and FAD.

14. The method for measuring the plasma levels of an inhibitor of $(Na^+ +K^+)$ATPase associated with hypertension as in claim 9, wherein said coenzyme is NADH.

15. The method for measuring the plasma levels of an inhibitor of $(Na^+ +K^+)$ATPase associated with hypertension as in claim 9, wherein said measuring of the concentration of said coenzyme or any other substance employed therewith whose spectroscopic properties are changed during the reaction is measured by ultraviolet or visible light absorbance at an appropriate absorbance wavelength of said coenzyme or substance.

16. The method for measuring the plasma levels of an inhibitor of $(Na^+ +K^+)$ATPase associated with hypertension as in claim 1, wherein said $(Na^+ +K^+)$ATPase assay solution additionally comprises (b) an enzymatic ATP coupled oxidation-reduction reaction system, and (c) an enzymatic ATP regenerating reaction system; and the method comprises following the activity of $(Na^+ +K^+)$ATPase by following changes in the enzymatic ATP coupled oxidation-reduction reaction system by measuring the concentration of a coenzyme or any other substance employed therewith whose spectroscopic properties are changed during the reaction.

17. The method for measuring the plasma levels of an inhibitor of $(Na^+ + K^+)$ATPase associated with hypertension as in claim 16, wherein said (a) $(Na^+ + K^+)$ATPase is selected from the group consisting of canine kidney $(Na^+ + K^+)$ATPase, bovine kidney $(Na^+ + K^+)$ATPase, porcine kidney $(Na^+ + K^+)$ATPase, bovine brain $(Na^+ + K^+)$ATPase, shark $(Na^+ + K^+)$ATPase, eel $(Na^+ + K^+)$ATPase and shrimp $(Na^+ + K^+)$ATPase.

18. The method for measuring the plasma levels of an inhibitor of $(Na^+ + K^+)$ATPase associated with hypertension as in claim 16, wherein said (a) $(Na^+ + K^+)$ATPase is canine kidney $(Na^+ + K^+)$ATPase.

19. The method for measuring the plasma levels of an inhibitor of $(Na^+ + K^+)$ATPase associated with hypertension as in claim 16, wherein said enzymatic ATP coupled oxidation-reduction reaction system (b) is selected from the group consisting of pyruvate-lactate dehydrogenase, pyruvate-pyruvate decarboxylase, acetaldehyde-alcohol dehydrogenase, pyruvate-pyruvate dehydrogenase, and glyceraldehyde-3-phosphate-glyceraldehyde-phosphate dehydrogenase.

20. The method for measuring the plasma levels of an inhibitor of $(Na^+ + K^+)$ATPase associated with hypertension as in claim 16, wherein said enzymatic ATP coupled oxidation-reduction system (b) is pyruvate-lactate dehydrogenase.

21. The method for measuring the plasma levels of an inhibitor of $(Na^+ + K^+)$ATPase associated with hypertension as in claim 16, wherein said enzymatic ATP regenerating reaction system (c) is selected from the group consisting of phosphoenolpyruvate-pyruvate kinase and 1,3-diphosphoglycerate-3-phosphoglycerate kinase.

22. The method for measuring the plasma levels of an inhibitor of $(Na^+ + K^+)$ATPase associated with hypertension as in claim 16, wherein said ATP regenerating reaction system (c) is phosphoenolpyruvate-pyruvate kinase.

23. The method for measuring the plasma levels of an inhibitor of $(Na^+ + K^+)$ATPase associated with hypertension as in claim 16, wherein said coenzyme is selected from the group consisting of NADH, NAD, NADPH, NADP, and FAD.

24. The method for measuring the plasma levels of an inhibitor of $(Na^+ + K^+)$ATPase associated with hypertension as in claim 16, wherein said coenzyme is NADH.

25. The method for measuring the plasma levels of an inhibitor of $(Na^+ + K^+)$ATPase associated with hypertension as in claim 16, wherein said measuring of the concentration of said coenzyme or any other substance employed therewith whose spectroscopic properties are changed during the reaction is measured by ultraviolet or visible light absorbance at an appropriate absorbance wavelength of said coenzyme or substance.

26. A method for diagnosing hypertension comprising:
  (1) incubating a deproteinized plasma sample from a patient in a $(Na^+ + K^+)$ATPase assay solution comprising ATP and (a) $(Na^+ + K^+)$ATPase;
  (2) following the activity of the $(Na^+ + K^+)$ATPase over the course of time; and
  (3) comparing the $(Na^+ + K^+)$ATPase activity in step (2) with the $(Na^+ + K^+)$ATPase activity of a standard so as to diagnose the presence or absence of hypertension.

27. The method for diagnosing hypertension as in claim 26, wherein said standard comprises the $(Na^+ + K^+)$ATPase activity determined for plasma of normotensive persons, with or without the addition of at least one inhibitor of $(Na^+ + K^+)$ATPase, by conducting steps (1) and (2).

28. The method for diagnosing hypertension as in claim 26, wherein said standard comprises the $(Na^+ + K^+)$ATPase activity determined for an artificial plasma saline solution, with or without the addition of at least one inhibitor of $(Na^+ + K^+)$ATPase.

29. The method for diagnosing hypertension as in claim 27, wherein said inhibitor is selected from the group consisting of ouabain, vanadate, quercetin and N-ethylmaleimide.

30. The method for diagnosing hypertension as in claim 28, wherein said inhibitor is selected from the group consisting of ouabain, vanadate, quercetin and N-ethylmaleimide.

31. The method for diagnosing hypertension as in claim 26, wherein said (a) $(Na^+ + K^+)$ATPase is selected from the group consisting of canine kidney $(Na^+ + K^+)$ATPase, bovine kidney $(Na^+ + K^+)$ATPase, porcine kidney $(Na^+ + K^+)$ATPase, bovine brain $(Na^+ + K^+)$ATPase, shark $(Na^+ + K^+)$ATPase, eel $(Na^+ + K^+)$ATPase and shrimp $(Na^+ + K^+)$ATPase.

32. The method for diagnosing hypertension as in claim 26, wherein said (a) $(Na^+ + K^+)$ATPase is canine kidney $(Na^+ + K^+)$ATPase.

33. The method for diagnosing hypertension as in claim 26, wherein the activity of (a) $(Na^+ + K^+)$ATPase is followed by measuring the release of inorganic phosphate as a consequence of ATP hydrolysis.

34. The method for diagnosing hypertension as in claim 33, wherein the release of inorganic phosphate as a consequence of ATP hydrolysis is followed using $\gamma$-$^{32}$Pi-labelled ATP and measuring the liberated $^{32}$Pi.

35. The method for diagnosing hypertension as in claim 33, wherein the release of inorganic phosphate as a consequence of ATP hydrolysis is followed by a colorimetric assay.

36. The method for diagnosing hypertension as in claim 33, wherein said (a) $(Na^+ + K^+)$ATPase is selected from the group consisting of canine kidney $(Na^+ + K^+)$ATPase, bovine kidney $(Na^+ + K^+)$ATPase, porcine kidney $(Na^+ + K^+)$ATPase, bovine brain $(Na^+ + K^+)$ATPase, shark $(Na^+ + K^+)$ATPase, eel $(Na^+ + K^+)$ATPase and shrimp $(Na^+ + K^+)$ATPase.

37. The method for diagnosing hypertension as in claim 33, wherein said (a) $(Na^+ + K^+)$ATPase is canine kidney $(Na^+ + K^+)$ATPase.

38. The method for diagnosing hypertension as in claim 26, wherein said $(Na^+ + K^+)$ATPase assay solution additionally comprises (b) an enzymatic ATP coupled oxidation-reduction reaction system; and the method comprises following the activity of $(Na^+ + K^+)$ATPase by following changes in the enzymatic ATP coupled oxidation-reduction reaction system by measuring the concentration of a coenzyme or any other substance employed therewith whose spectroscopic properties are changed during the reaction.

39. The method for diagnosing hypertension as in claim 38, wherein said (a) $(Na^+ + K^+)$ATPase is selected from the group consisting of canine kidney $(Na^+ + K^+)$ATPase, bovine kidney $(Na^+ + K^+)$ATPase, porcine kidney $(Na^+ + K^+)$ATPase, bovine brain $(Na^+ + K^+)$ATPase, shark $(Na^+ + K^+)$ATPase, eel $(Na^+ + K^+)$ATPase and shrimp $(Na^+ + K^+)$ATPase.

40. The method for diagnosing hypertension as in claim 38, wherein said (a) $(Na^+ + K^+)$ATPase is canine kidney $(Na^+ + K^+)$ATPase.

41. The method for diagnosing hypertension as in claim 38, wherein said enzymatic ATP coupled oxidation-reduction reaction system (b) is glyceraldehyde-3-phosphate-glyceraldehyde-phosphate dehydrogenase.

42. The method for diagnosing hypertension as in claim 38, wherein said coenzyme is selected from the group consisting of NADH, NAD, NADPH, NADP, and FAD.

43. The method for diagnosing hypertension as in claim 38, wherein said coenzyme is NADH.

44. The method for diagnosing hypertension as in claim 38, wherein said measuring of the concentration of said coenzyme or any other substance employed therewith whose spectroscopic properties are changed during the reaction is measured by ultraviolet or visible light absorbance at an appropriate absorbance wavelength of said coenzyme or substance.

45. The method for diagnosing hypertension as in claim 26, wherein said $(Na^+ + K^+)$ATPase assay solution additionally comprises (b) an enzymatic ATP coupled oxidation-reduction reaction system, and (c) an enzymatic ATP regenerating reaction system; and the method comprises following the activity of $(Na^+ + K^+)$ATPase by following changes in the enzymatic ATP coupled oxidation-reduction reaction system by measuring the concentration of a coenzyme or any other substance employed therewith whose spectroscopic properties are changed during the reaction.

46. The method for diagnosing hypertension as in claim 45, wherein said (a) $(Na^+ + K^+)$ATPase is selected from the group consisting of canine kidney $(Na^+ + K^+)$ATPase, bovine kidney $(Na^+ + K^+)$ATPase, porcine kidney $(Na^+ + K^+)$ATPase, bovine brain $(Na^+ + K^+)$ATPase, shark $(Na^+ + K^+)$ATPase, eel $(Na^+ + K^+)$ATPase and shrimp $(Na^+ + K^+)$ATPase.

47. The method for diagnosing hypertension as in claim 45, wherein said (a) $(Na^+ + K^+)$ATPase is canine kidney $(Na^+ + K^+)$ATPase.

48. The method for diagnosing hypertension as in claim 45, wherein said enzymatic ATP coupled oxidation-reduction reaction system (b) is selected from the group consisting of pyruvate-lactate dehydrogenase, pyruvate-pyruvate decarboxylase, acetaldehyde-alcohol dehydrogenase, pyruvate-pyruvate dehydrogenase, and glyceraldehyde-3-phosphate-glyceraldehyde-phosphate dehydrogenase.

49. The method for diagnosing hypertension as in claim 45, wherein said enzymatic ATP coupled oxidation-reduction system (b) is pyruvate-lactate dehydrogenase.

50. The method for diagnosing hypertension as in claim 45, wherein said enzymatic ATP regenerating reaction system (c) is selected from the group consisting of phosphoenolpyruvate-pyruvate kinase and 1,3-diphosphoglycerate-phosphoglycerate kinase.

51. The method for diagnosing hypertension as in claim 45, wherein said ATP regenerating reaction system (c) is phosphoenolpyruvate-pyruvate kinase.

52. The method for diagnosing hypertension as in claim 45, wherein said coenzyme is selected from the group consisting of NADH, NAD, NADPH, NADP, and FAD.

53. The method for diagnosing hypertension as in claim 45, wherein said coenzyme is NADH.

54. The method for diagnosing hypertension as in claim 45, wherein said measuring of the concentration of said coenzyme or any other substance employed therewith whose spectroscopic properties are changed during the reaction is measured by ultraviolet or visible light absorbance at an appropriate absorbance wavelength of said coenzyme or substance.

55. A method for monitoring antihypertensive therapy comprising:
   (1) incubating a deproteinized plasma sample from a hypertensive patient in a $(Na^+ + K^+)$ATPase assay solution comprising ATP and (a) $(Na^+ + K^+)$ATPase;
   (2) following the activity of the $(Na^+ + K^+)$ATPase over the course of time;
   (3) comparing the $(Na^+ + K^+)$ATPase activity of step (2) with the $(Na^+ + K^+)$ATPase activity of a standard; and
   (4) repeating steps (1)–(3) at suitable time intervals after the initiation of antihypertensive therapy and monitoring the activity of the $(Na^+ + K^+)$ATPase activity at each time interval so as to monitor the effect of said antihypertensive therapy.

56. The method for monitoring antihypertensive therapy as in claim 55, wherein said standard comprises the $(Na^+ + K^+)$ATPase activity determined for plasma of normotensive persons, with or without the addition of at least one inhibitor of $(Na^+ + K^+)$ATPase, by conducting steps (1) and (2).

57. The method for monitoring antihypertensive therapy as in claim 55, wherein said standard comprises the $(Na^+ + K^+)$ATPase activity determined for an artificial plasma saline solution, with or without the addition of at least one inhibitor of $(Na^+ + K^+)$ATPase.

58. The method for monitoring antihypertensive therapy as in claim 56, wherein said inhibitor is selected from the group consisting of ouabain, vanadate, quercetin and N-ethyl-maleimide.

59. The method for monitoring antihypertensive therapy as in claim 57, wherein said inhibitor is selected from the group consisting of ouabain and vanadate, quercetin and N-ethyl-maleimide.

60. The method for monitoring antihypertensive therapy as in claim 55, wherein said (a) $(Na^+ + K^+)$ATPase is selected from the group consisting of canine kidney $(Na^+ + K^+)$ATPase, bovine kidney $(Na^+ + K^+)$ATPase, porcine kidney $(Na^+ + K^+)$ATPase, bovine brain $(Na^+ + K^+)$ATPase, shark $(Na^+ + K^+)$ATPase, eel $(Na^+ + K^+)$ATPase and shrimp $(Na^+ + K^+)$ATPase.

61. The method for monitoring antihypertensive therapy as in claim 55, wherein said (a) $(Na^+ + K^+)$ATPase is canine kidney $(Na^+ + K^+)$ATPase.

62. The method for monitoring antihypertensive therapy as in claim 55, wherein the activity of (a) $(Na^+ + K^+)$ATPase is followed by measuring the release of inorganic phosphate as a consequence of ATP hydrolysis.

63. The method for monitoring antihypertensive therapy as in claim 62, wherein the release of inorganic phosphate as a consequence of ATP hydrolysis is followed using $\gamma$-$^{32}$Pi-labelled ATP and measuring the liberated $^{32}$Pi.

64. The method for monitoring antihypertensive therapy as in claim 62, wherein the release of inorganic phosphate as a consequence of ATP hydrolysis is followed by a colorimetric assay.

65. The method for monitoring antihypertensive therapy as in claim 62, wherein said (a) $(Na^+ + K^+)$ATPase is selected from the group consisting of canine kidney $(Na^+ + K^+)$ATPase, bovine kidney $(Na^+ + K^+)$ATPase, porcine kidney $(Na^+ + K^+)$ATPase, bovine brain $(Na^+ + K^+)$ATPase, shark $(Na^+ + K^+)$ATPase, eel $(Na^+ + K^+)$ATPase and shrimp $(Na^+ + K^+)$ATPase.

66. The method for monitoring antihypertensive therapy as in claim 62, wherein said (a) $(Na^+ + K^+)$ATPase is canine kidney $(Na^+ + K^+)$ATPase.

67. The method for monitoring antihypertensive therapy as in claim 55, wherein said $(Na^+ + K^+)$ATPase assay solution additionally comprises (b) an enzymatic ATP coupled oxidation-reduction reaction system; and the method comprises following the activity of $(Na^+ + K^+)$ATPase by following changes in the enzymatic ATP coupled oxidation-reduction reaction system by measuring the concentration of a coenzyme or any other substance employed therewith whose spectroscopic properties are changed during the reaction.

68. The method for monitoring antihypertensive therapy as in claim 67, wherein said (a) $(Na^+ + K^+)$ATPase is selected from the group consisting of canine kidney $(Na^+ + K^+)$ATPase, bovine kidney $(Na^+ + K^+)$ATPase, porcine kidney $(Na^+ + K^+)$ATPase, bovine brain $(Na^+ + K^+)$ATPase, shark $(Na^+ + K^+)$ATPase, eel $(Na^+ + K^+)$ATPase and shrimp $(Na^+ + K^+)$ATPase.

69. The method for monitoring antihypertensive therapy as in claim 67, wherein said (a) $(Na^+ + K^+)$ATPase is canine kidney $(Na^+ + K^+)$ATPase.

70. The method for monitoring antihypertensive therapy as in claim 67, wherein said enzymatic ATP coupled oxidation-reduction reaction system (b) is glyceraldehyde-3-phosphate-glyceraldehyde-phosphate dehydrogenase.

71. The method for monitoring antihypertensive therapy as in claim 67, wherein said coenzyme is selected from the group consisting of NADH, NAD, NADPH, NADP, and FAD.

72. The method for monitoring antihypertensive therapy as in claim 67, wherein said coenzyme is NADH.

73. The method for monitoring antihypertensive therapy as in claim 67, wherein said measuring of the concentration of said coenzyme or any other substance employed therewith whose spectroscopic properties are changed during the reaction is measured by ultraviolet or visible light absorbance at an appropriate absorbance wavelength of said coenzyme or substance.

74. The method for monitoring antihypertensive therapy as in claim 55, wherein said $(Na^+ + K^+)$ATPase assay solution additionally comprises (b) an enzymatic ATP coupled oxidation-reduction reaction system, and (c) an enzymatic ATP regenerating reaction system; and the method comprises following the activity of $(Na^+ + K^+)$ATPase by following changes in the enzymatic ATP coupled oxidation-reduction reaction system by measuring the concentration of a coenzyme or any other substance employed therewith whose spectroscopic properties are changed during the reaction.

75. The method for monitoring antihypertensive therapy as in claim 74, wherein said (a) $(Na^+ + K^+)$ATPase is selected from the group consisting of canine kidney $(Na^+ + K^+)$ATPase, bovine kidney $(Na^+ + K^+)$ATPase, porcine kidney $(Na^+ + K^+)$ATPase, bovine brain $(Na^+ + K^+)$ATPase, shark $(Na^+ + K^+)$ATPase, eel $(Na^+ + K^+)$ATPase and shrimp $(Na^+ + K^+)$ATPase.

76. The method for monitoring antihypertensive therapy as in claim 74, wherein said (a) $(Na^+ + K^+)$ATPase is canine kidney $(Na^+ + K^+)$ATPase.

77. The method for monitoring antihypertensive therapy as in claim 74, wherein said enzymatic ATP coupled oxidation-reduction reaction system (b) is selected from the group consisting of pyruvate-lactate dehydrogenase, pyruvate-pyruvate decarboxylase, acetaldehyde-alcohol dehydrogenase, pyruvate-pyruvate dehydrogenase, and glyceraldehyde-3-phosphate-glyceraldehyde-phosphate dehydrogenase.

78. The method for monitoring antihypertensive therapy as in claim 74, wherein said enzymatic ATP coupled oxidation-reduction system (b) is pyruvate-lactate dehydrogenase.

79. The method for monitoring antihypertensive therapy as in claim 74, wherein said enzymatic ATP regenerating reaction system (c) is selected from the group consisting of phosphoenolpyruvate-pyruvate kinase and 1,3-diphosphoglycerate-phosphoglycerate kinase.

80. The method for monitoring antihypertensive therapy as in claim 74, wherein said ATP regenerating reaction system (c) is phosphoenolpyruvate-pyruvate kinase.

81. The method for monitoring antihypertensive therapy as in claim 74, wherein said coenzyme is selected from the group consisting of NADH, NAD, NADPH, NADP, and FAD.

82. The method for monitoring antihypertensive therapy as in claim 74, wherein said coenzyme is NADH.

83. The method for monitoring antihypertensive therapy as in claim 74, wherein said measuring of the concentration of said coenzyme or any other substance employed therewith whose spectroscopic properties are changed during the reaction is measured by ultraviolet or visible light absorbance at an appropriate absorbance wavelength of said coenzyme or substance.

* * * * *